US00PP25476P3

(12) United States Plant Patent
Kardos

(10) Patent No.: US PP25,476 P3
(45) Date of Patent: Apr. 28, 2015

(54) ***LAGERSTROEMIA* PLANT NAMED 'PIILAG B5'**

(50) Latin Name: ***Lagerstroemia indica*×L. *fauriei***
Varietal Denomination: PIILAG B5

(71) Applicant: Joshua H. Kardos, Watkinsville, GA (US)

(72) Inventor: Joshua H. Kardos, Watkinsville, GA (US)

(73) Assignee: Plant Introductions, Inc., Watkinsville, GA (US)

( * ) Notice: Subject to any disclaimer, the term of this patent is extended or adjusted under 35 U.S.C. 154(b) by 0 days.

(21) Appl. No.: 13/815,401

(22) Filed: Feb. 28, 2013

(65) Prior Publication Data

US 2014/0245504 P1 Aug. 28, 2014

(51) Int. Cl.
*A01H 5/00* (2006.01)

(52) U.S. Cl.
USPC ..... Plt./252

(58) Field of Classification Search
USPC ..... Plt./252
See application file for complete search history.

(56) References Cited

U.S. PATENT DOCUMENTS

| | | | |
|---|---|---|---|
| PP10,319 | P | 4/1998 | Whitcomb |
| PP16,917 | P2 | 8/2006 | Dirr |
| PP17,411 | P2 | 2/2007 | Dirr |
| PP21,540 | P2 | 11/2010 | Knight |
| PP22,161 | P2 | 9/2011 | Dirr |
| PP23,071 | P3 | 9/2012 | Dirr |
| PP23,168 | P3 | 11/2012 | Griffith |
| PP23,178 | P3 | 11/2012 | Dirr |
| PP23,518 | P3 | 4/2013 | Kardos |
| 2013/0125275 | P1 | 5/2013 | Kardos |
| 2013/0125276 | P1 | 5/2013 | Kardos |

OTHER PUBLICATIONS

First Editions Collection webpage, (downloaded Mar. 6, 2013, available on Internet in Jan. 2013), "*Lagerstroemia* 'PIILAG-IV'", http://www_._firsteditionsplants_._com_/collection, 1 page.
First Editions Collection webpage, (downloaded Mar. 6, 2013, available on Internet in Jan. 2013), "*Lagerstroemia* 'PIILAG-V'", http://www_._firsteditionsplants_._com_/collection, 1 page.
American Nurseryman Catalog, "2013_AN_Woody Plants," Dec. 2012, p. W5.

*Primary Examiner* — Kent L Bell
(74) *Attorney, Agent, or Firm* — Lathrop & Gage LLP

(57) ABSTRACT

A new and distinct cultivar of *Lagerstroemia* plant named 'PIILAG B5', characterized by its compact, upright, intermediate growth habit, reddish new growth, lustrous dark green foliage in summer, red flowers, and resistance to powdery mildew and *Cercospora* leaf spot.

2 Drawing Sheets

Genus and species of plant claimed: *Lagerstroemia indica*×L. *fauriei*.

Variety denomination: 'PIILAG B5'.

BACKGROUND OF THE INVENTION

The present invention relates to a new and distinct cultivar of *Lagerstroemia* plant, botanically known as *Lagerstroemia indica*×L. *fauriei*, commonly known as crapemyrtle, and hereinafter referred to by the cultivar name 'PIILAG B5'. 'PIILAG B5' is grown primarily as an ornamental for landscape use and for use as a potted plant.

'PIILAG B5' originated from open-pollinated seed of *Lagerstroemia indica*×L. *fauriei* 'PIILAG-III' (U.S. Plant Pat. No. 23,178) growing in Watkinsville, Ga. The cultivar 'PIILAG B5' originated in 2009 and was selected in a cultivated environment in Watkinsville, Ga. from the progeny of this open-pollination by continued evaluation for growth habit and foliage and flower characteristics.

Asexual reproduction of 'PIILAG B5' by stem cuttings in Watkinsville, Ga. since 2010 has shown that all the unique features of this new *Lagerstroemia,* as herein described, are stable and reproduced true-to-type through successive generations of such asexual propagation.

SUMMARY OF THE INVENTION

Plants of the new cultivar 'PIILAG B5' have not been observed under all possible environmental conditions. The phenotype may vary somewhat with changes in light, temperature, soil and rainfall without, however, any variance in genotype.

The following traits have been repeatedly observed and are determined to be unique characteristics of 'PIILAG B5'. These characteristics in combination distinguish 'PIILAG B5' as a new and distinct cultivar:

1. Compact, upright, intermediate growth habit;
2. Reddish new growth;
3. Lustrous dark green foliage in summer;
4. Red flowers;
5. Resistance to powdery mildew and *Cercospora* leaf spot.

Plants of 'PIILAG B5' differ from plants of the parent, primarily in foliage size and color, flower color, and disease resistance. Plants of 'PIILAG-III' have red-purple new growth, dark red flowers and moderate resistance to *Cercospora* leaf spot, whereas plants of 'PIILAG B5' have overall smaller foliage with reddish new growth, lighter red flowers, and improved resistance to *Cercospora* leaf spot.

Plants of 'PIILAG B5' can be compared to the cultivar 'Gamad I' (U.S. Plant Pat. No. 16,917), but differ in growth habit and overall size and flowering time. Plants of 'PIILAG B5' have a compact, upright, intermediate growth habit and flowers in mid-summer, whereas plants of 'Gamad I' have an overall smaller, mounded growth habit and flowers in late summer.

BRIEF DESCRIPTION OF THE DRAWINGS

The accompanying color photographs illustrate the flower and foliage characteristics and the overall appearance of 'PIILAG B5', showing the colors as true as it is reasonably possible to obtain in color reproductions of this type. Colors in the photographs may differ slightly from the color values cited in the detailed botanical description which accurately describe the colors of the new *Lagerstroemia*.

DETAILED DESCRIPTION

Figure 1:
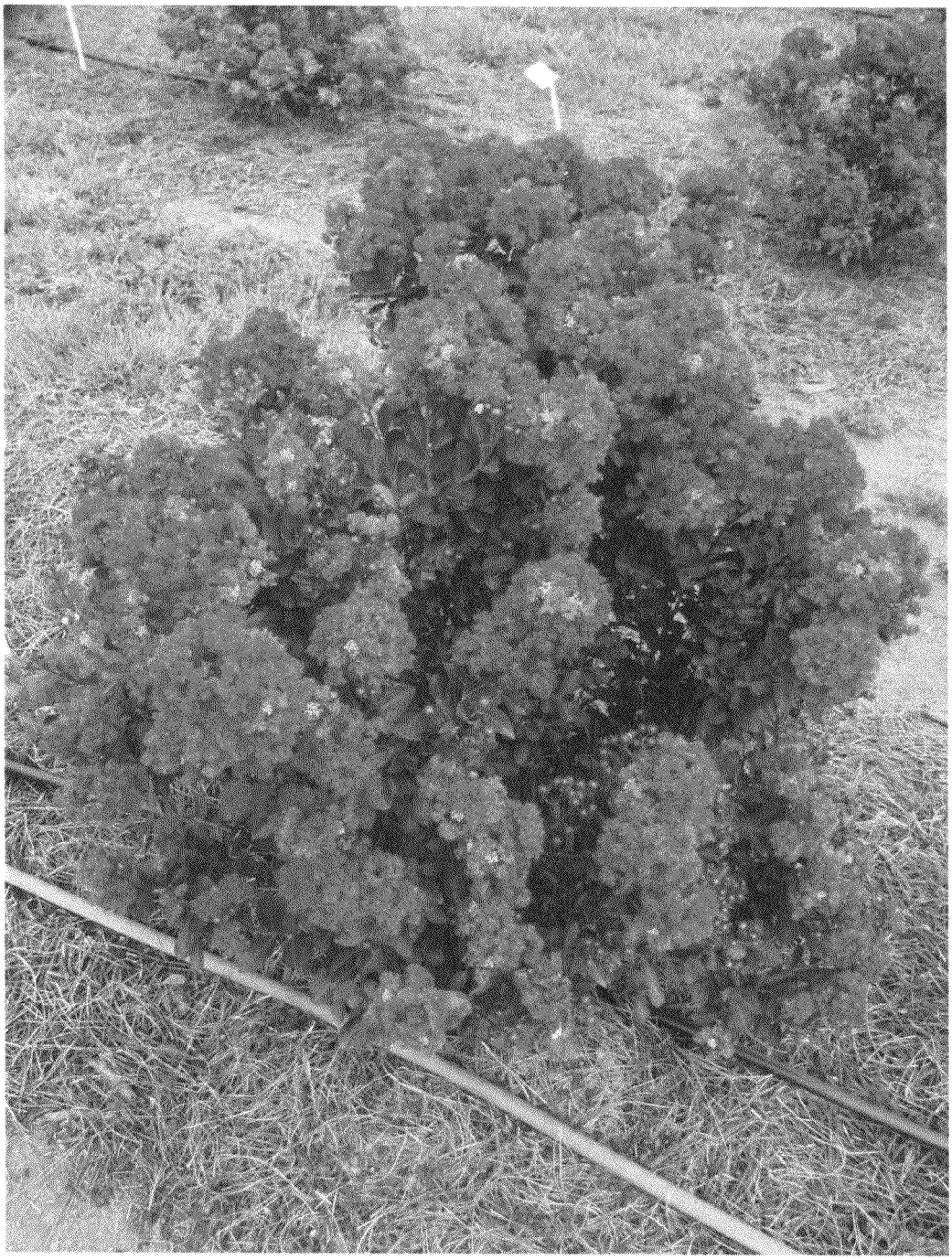
FIG. 1 illustrates the overall appearance of an established plant of 'PIILAG B5' planted in the ground.
Figure 2:
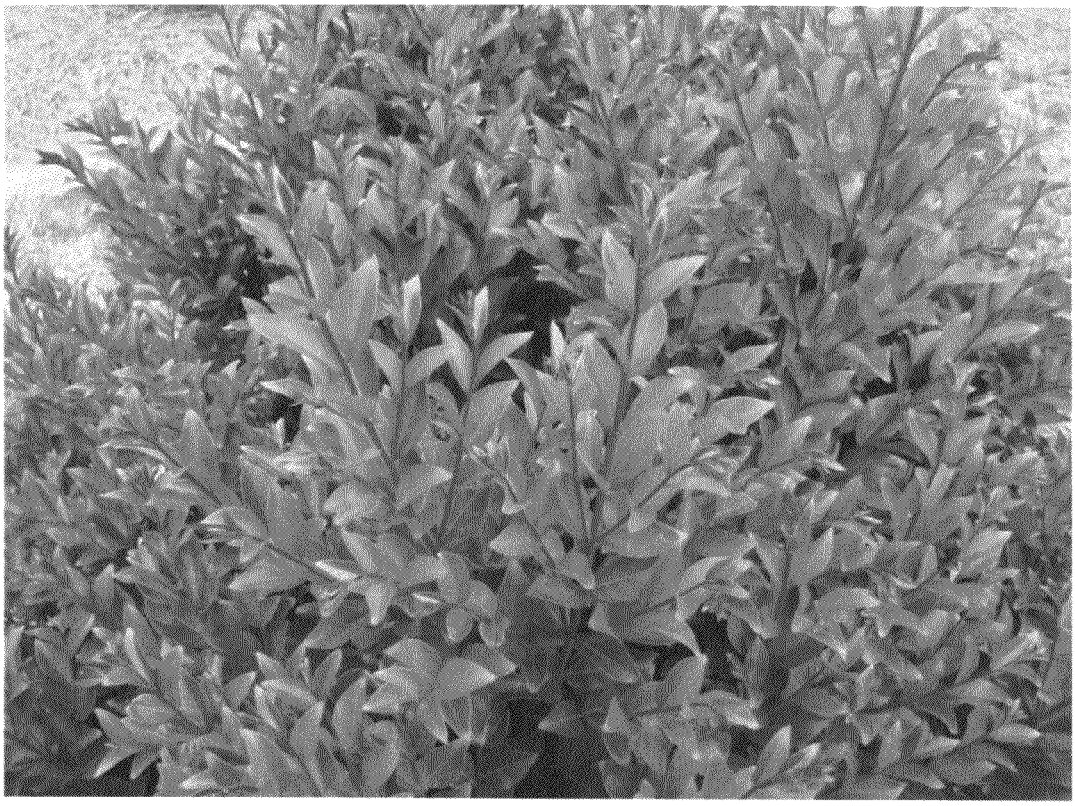
FIG. 2 illustrates a close-up view of the new growth of 'PIILAG B5'.

In the following description, color references are made to The Royal Horticultural Society Colour Chart, 2007 Edition, except where general terms of ordinary dictionary significance are used. Plants used for the description were approximately two years old and were grown in 11.8 L containers under outdoor conditions in Watkinsville, Ga. Colors are described using The Royal Horticultural Society Colour Chart (R.H.S.).

Botanical classification: *Lagerstroemia* L., cultivar 'PIILAG B5'.

Parentage:

*Female, or seed, parent.*—*Lagerstroemia* 'PIILAG-III' (U.S. Plant Pat. No. 23,178).

*Male, or pollen parent.*—Unknown (open-pollinated).

Propagation: Terminal cuttings.

*Time to initiate roots, summer.*—About 21 days at 32° C.

Plant description: Flowering shrub; compact, upright, intermediate growth habit. Freely branching; lateral branches abundant without pruning, resulting in fine-textured, dense habit.

*Root description.*—Numerous, fine, fibrous and well-branched.

*Plant size.*—The original plant, now about four-years-old in the ground, is about 142 cm high from the soil level to the top of the inflorescences and about 127 cm wide. First year stems have a diameter of about 2.5 mm. First year stems have length of 30.48 cm to 45.75 cm. Shape: squarish. Second year and older stems have a diameter of about 5 mm or more. Second year stems have length of 60.96 cm to 91.44 cm. Shape: round.

*Trunk diameter.*—3.5 cm at the soil line. Color: N199B.

*Internode length.*—About 2 cm.

*Strength.*—Flexible when young, easily broken once mature.

*First year stem color* (*young*).—179B. Color (woody): 200D.

*Second year and older stem color.*—N199B.

*Bark.*—Exfoliates in strips beginning on second or third year stems.

Vegetative buds: Sub-opposite to alternate in arrangement, imbricate, conical, with no pubescence.

*Color.*—179B.

*Size.*—About 2.5 mm in length and 1 mm in width.

Foliage description:

*Arrangement.*—Sub-opposite to alternate, simple.

*Length.*—About 4.4 cm.

*Width.*—About 3 cm.

*Shape.*—Elliptical.

*Apex.*—Acuminate.

*Base.*—Cuneate.

*Margin.*—Entire.

*Texture* (*upper and lower surfaces*).—Glabrous and glossy.

*Venation pattern.*—Pinnate.

*Venation color of emerging foliage* (*upper and lower surfaces*).—180A.

*Venation color of fully expanded foliage* (*upper and lower surfaces*).—173C.

*Color in developing foliage* (*upper and lower surfaces*) .—180A.

*Color in fully expanded foliage* (*upper surface*).—147A.

*Color in fully expanded foliage* (*lower surface*).—146A.

*Petiole length.*—About 2 mm.

*Petiole diameter.*—About 1 mm.

*Petiole color* (*upper and lower surfaces*).—179B.

*Pubescence.*—None.

Flower description: Flowers are produced from about June to September in Watkinsville, Ga. An inflorescence is showy for about two weeks, and individual flowers last about one day and are self-cleaning. Flowers are lightly fragrant.

*Inflorescence type.*—Panicle. Panicle contains between 20 to 150 buds or flowers.

*Inflorescence length.*—About 10.6 cm.

*Inflorescence width.*—About 9.4 cm.

*Peduncle.*—About 8.6 cm in length, about 2 mm in diameter, color is 179B, and no pubescence.

*Individual flowers.*—About 2.3 cm in height and 3 cm in diameter.

*Flower buds.*—Length: about 8 mm; Diameter: about 8 mm; Color: 46B. Unopened flower buds are globose with six distinct lines of dehiscence where they split to reveal the flower.

*Sepals.*—Arrangement/quantity: single whorl of six fused sepals. Length about 9 mm. Width: about 4 mm. Shape: elliptical. Apex: acute. Margin: entire. Texture, upper and lower surfaces: smooth, glabrous. Color when opening, upper surface: 163D. When opening lower surface: 179A. Fully opened, upper surface: 163D. Fully opened, lower surface: 179A.

*Pedicels.*—About 8 mm in length, about 1 mm in diameter, 179B in color, and no pubescence.

*Calyx.*—About 8 mm in length, about 1 cm in diameter, 46C in color on both surfaces, and no pubescence.

Petals:

*Arrangement/appearance.*—Usually 6 or 7 per flower.

*Petal length.*—About 1.5 cm.

*Petal width.*—About 1.3 cm.

*Petal shape.*—Fan-shaped.

*Petal apex.*—Ruffled, rounded.

*Petal base.*—Sagittate.

*Petal margin.*—Undulate.

*Petal texture* (*upper and lower surfaces*).—Glabrous.

*Petal color.*—Upper and lower surfaces are 53B.

Stamens:

*Quantity/arrangement.*—About 25 to 30 short stamens clustered in the center, about 8 mm long, filament color is 49A, and anther color is 13A. The short stamens are surrounded by 6 longer stamens, about 1.4 cm long, filament color is 52B, and anther color is 13A. The stamens are not pubescent.

*Pollen*.—Produced in moderate quantities and is 7B in color on the short and long stamens.

Pistils:

*Quantity*.—One superior pistil per flower.

*Pubescence*.—None.

*Pistil length*.—About 1.9 cm in length.

*Stigma shape*.—Round, about 1 mm in diameter.

*Stigma color*.—N144D.

*Style color*.—47C and about 1.5 cm in length.

*Ovary color*.—10B and about 2.5 mm in diameter.

Fruit:

*Type/appearance*.—Six-valved, dehiscent, broad ellipsoidal capsule.

*Length*.—About 8 mm.

*Diameter*.—About 8 mm.

*Immature color*.—144A.

*Mature color*.—200C. Each capsule contains many seeds that are about 5 mm long, 3 mm wide, and 200C in color.

Plant hardiness:

*Plant hardiness*.—USDA Plant Hardiness Zone Map (2012): Zone 6 to 9.

Disease/pest resistance: Plants of the claimed *Lagerstroemia* variety grown in field and container trials have exhibited resistance to powdery mildew and *Cercospora* leaf spot.

I claim:

1. A new and distinct *Lagerstroemia* plant named 'PIILAG B5', as illustrated and described herein.

* * * * *